United States Patent
Brieva et al.

(10) Patent No.: US 8,956,668 B2
(45) Date of Patent: Feb. 17, 2015

(54) COSMETIC COMPOSITION COMPRISING A HYDRATING ACTIVE INGREDIENT

(75) Inventors: Patricia Brieva, Manalapan, NJ (US); Angelike Galdi, Westfield, NJ (US)

(73) Assignee: L'Oreal, Paris (FR)

(*) Notice: Subject to any disclaimer, the term of this patent is extended or adjusted under 35 U.S.C. 154(b) by 300 days.

(21) Appl. No.: 13/467,656

(22) Filed: May 9, 2012

(65) Prior Publication Data

US 2013/0302452 A1  Nov. 14, 2013

(51) Int. Cl.
*A61K 36/886* (2006.01)
*A61K 36/00* (2006.01)

(52) U.S. Cl.
USPC ............................ 424/744; 424/725; 424/774

(58) Field of Classification Search
None
See application file for complete search history.

(56) References Cited

U.S. PATENT DOCUMENTS

| | | | |
|---|---|---|---|
| 5,980,921 A | 11/1999 | Biedermann et al. | |
| 6,589,514 B2 * | 7/2003 | Jensen et al. | 424/59 |
| 7,731,982 B2 * | 6/2010 | Schroder | 424/401 |
| 2007/0297999 A1 | 12/2007 | Fonolla Moreno et al. | |
| 2009/0104174 A1 * | 4/2009 | Smith | 424/94.63 |
| 2009/0270788 A1 * | 10/2009 | Marenus et al. | 604/20 |
| 2010/0047295 A1 * | 2/2010 | Giagnorio | 424/401 |

FOREIGN PATENT DOCUMENTS

| | | | |
|---|---|---|---|
| JP | 2005060253 A | * | 3/2005 |
| WO | 2009085472 A1 | | 7/2009 |

* cited by examiner

*Primary Examiner* — Qiuwen Mi
(74) *Attorney, Agent, or Firm* — McNees, Wallace & Nurick, LLC

(57) ABSTRACT

A cosmetic composition in the form of an emulsion and a cold-processing method for preparing the cosmetic composition are provided. The cosmetic composition includes a hydrating active ingredient, at least one gelling agent, and at least one thickener. The hydrating active ingredient is present at a concentration, by weight, of about 0.1% to about 90%, based upon weight of the composition. The at least one gelling agent is present at a concentration, by weight, of about 0.01% to about 5%, based upon weight of the composition. The at least one thickener is present at a concentration, by weight of about 0.1% to about 5%, based upon weight of the composition.

11 Claims, No Drawings

COSMETIC COMPOSITION COMPRISING A HYDRATING ACTIVE INGREDIENT

FIELD OF THE INVENTION

The present invention is directed to cosmetic compositions and methods of using and producing cosmetic compositions. More specifically, the present invention is directed to a cosmetic composition in the form of an emulsion having hydrating active ingredient, at least one gelling agent, and at least one thickener.

BACKGROUND OF THE INVENTION

For various reasons associated in particular with greater comfort of use (softness, emollience and the like), current cosmetic compositions are usually in the form of an emulsion of the oil-in-water (O/W) type consisting of an aqueous-dispersing-continuous phase and an oily-dispersed-discontinuous phase, or of an emulsion of the water-in-oil (W/O) type consisting of an oily-dispersing-continuous phase and an aqueous-dispersed-discontinuous phase. O/W emulsions are preferred in the cosmetics field, because O/W emulsions comprise an aqueous phase as external phase, which gives the emulsions, when applied to the skin, a fresher, less greasy and lighter feel than W/O emulsions.

Challenges have been encountered in obtaining O/W emulsions including Aloe Barbadensis Leaf Juice or aloe vera juice compared to O/W emulsions including water. One of the reasons for difficulty in forming O/W emulsions including aloe vera juice is that aloe vera has different properties than water. More specifically, aloe vera juice has a different pH, different surface tension, and also includes amino acids that are not present in water. The surface tension of water is ~55.73 dyne/cm, based on temperature and purity level. In contrast, the surface tension of aloe vera juice is ~49.75 dyne/cm and pH is 4, based on temperature and purity level. The different material strength of Aloe vera, compared to water, results in a lower surface tension, making it harder to include in cosmetic formulations such as O/W emulsions. The amino acids present in aloe vera juice increase the difficulty in suspending the aloe vera juice in a thick cream, particularly when the juice is not suspended by heated emulsifiers and surfactants. Heating destroys some of the amino acids in the aloe vera, thereby decreasing the healing properties of aloe vera.

Most cosmetic compositions include preserving agents having antibacterial properties. Use of parabens as a preserving agent has received consumer scrutiny; however, paraben-free systems are difficult to formulate because paraben-free systems use preservatives that reduce emulsion stability and decrease viscosity of formulations.

A cosmetic composition and methods of using and producing cosmetic compositions in the form of cosmetic composition that do not suffer from one or more of the above drawbacks would be desirable in the art.

BRIEF DESCRIPTION OF THE INVENTION

In an exemplary embodiment, a cosmetic composition in the form of an emulsion is provided. The cosmetic composition includes a hydrating active ingredient, at least one gelling agent, and at least one thickener. The hydrating active ingredient is at a concentration, by weight, of about 0.1% to about 90%, based upon weight of the composition. The at least one gelling agent is at a concentration, by weight, of about 0.01% to about 5%, based upon weight of the composition. The at least one thickener is at a concentration, by weight of about 0.1% to about 5%, based upon weight of the composition.

In another exemplary embodiment, a method for preparing the cosmetic composition is provided. The method includes mixing a first phase including the hydrating active at ambient temperature. The method includes mixing a second phase including the at least one gelling-agent and at least one thickener at ambient temperature. The method includes homogenizing the mixed first phase and the mixed second phase forming an oil-in-water emulsion at ambient temperature. During the method of preparing the cosmetic composition, the temperature of the composition during mixing and homogenizing does not exceed about 30° C.

The present disclosure is also directed to a method for cosmetic treatment of keratinous tissues by applying the above-disclosed composition onto a surface of the keratinous tissue.

Other features and advantages of the present invention will be apparent from the following more detailed description of the preferred embodiment which illustrates, by way of example, the principles of the invention.

DETAILED DESCRIPTION OF THE INVENTION

"Keratinous tissue," as used herein, includes but is not limited to skin, hair, and nails.

"Homogenous" means substantially uniform throughout, i.e., a single phase mixture.

In the present application the term "ambient temperature" means a temperature of 25° C.

The cosmetic compositions and methods of the present invention can comprise, consist of, or consist essentially of the essential elements and limitations of the invention described herein, as well as any additional or optional ingredients, components, or limitations described herein or otherwise useful in personal care compositions intended for topical application to keratinous tissue.

It has been surprisingly discovered by the inventors that a stable cream including a hydrating active ingredient, aloe vera, at least one gelling agent, can be formed without emulsifiers, surfactants, and parabens, using a cold-processing method that is free from heat and at least one thickener is formed using cold processing.

Hydrating Active Ingredient

The hydrating active ingredient is at a concentration, by weight, of about 0.1% to about 90%, or alternatively about 10% to about 90% or alternatively about 25% to about 80%, based upon weight of the composition. In one embodiment, the hydrating active ingredient is aloe vera or INCI Aloe Barbadensis Leaf Juice.

In a preferred embodiment, the Aloe Barbadensis Leaf Juice used is 80% Aloe Vera Gel (1x) Decolorized from Terry Laboratories, Melbourne, Fla.

Gelling Agent

The gelling agent present in the cosmetic composition according to the present disclosure includes carbomer, acrylates/C10-30 alkyl acrylate crosspolymer, and combinations thereof. A suitable example of carbomer includes Carbomer, available from 3V of Sigma, Georgetown, S.C. Suitable example of acrylates/C10-30 alkyl acrylate crosspolymer includes CARBOPOL® Ultrez 20 Polymer, available from LUBRIZOL, Cleveland, Ohio.

The gelling agent is advantageously present at a concentration, by weight, of about 0.01% to about 5%, or alternatively about 0.05% to about 4%, or alternatively about 0.5% to about 3.0% based upon weight of the composition.

Thickener

The at least one thickener present in the cosmetic composition according to the present disclosure includes sodium acrylate/sodium acryloyldimethyl taurate copolymer, acrylamide/sodium acryloyldimethyltaurate copolymer, ammonium polyacryloyldimethyl taurate, ammonium acryloydimethyl taurate/VP copolymer, and combinations thereof.

In a preferred embodiment, the sodium acrylate/sodium acryloyldimethyl taurate copolymer is SIMULGEL® EG a sodium acrylate/sodium acryloyldimethyl taurate copolymer and isohexadecane and polysorbate 80, available from SEPPIC Inc., Fairfield, N.J.

The thickener is advantageously present at a concentration, by weight, of about 0.1% to about 5%, or alternatively about 0.5% to about 4%, or alternatively about 0.8% to about 3.5% based upon weight of the composition.

Arginine

The cosmetic composition further comprises arginine to serve as a neutralizer and to enhance moisture retention.

Arginine is advantageously present at a concentration, by weight, of about 0.05% to about 1.5%, or alternatively about 0.1% to about 1.3%, or alternatively about 0.2% to about 1.2% based upon weight of the composition The cosmetic composition of the present disclosure is devoid of parabens.

The cosmetic composition of the present disclosure is devoid of surfactants.

The cosmetic composition of the present disclosure is devoid of emulsifiers.

The cosmetic composition of the present disclosure has a viscosity at 25° C. of 25 milliPascal·seconds (mPa·s) to about 105 mPa·s, or alternatively about 40 mPa·s to about 100 mPa·s, or alternatively about 65 mPa·s to about 95 mPa·s. The viscosity was measured with a Viscometer Rheomat at 25° C. The viscosity of the cosmetic composition was measured with Spindle No. 3 at 200 rpm rotations per min at 25° C. for 10 minutes.

The cosmetic composition of the present disclosure forms an oil-in-water type emulsion using cold-processing methods and without the use of heat.

Aqueous Phase

The aqueous phase present in the cosmetic composition according to the disclosure includes a hydrating active ingredient, the hydrating active ingredient at a concentration, by weight, of about 0.1% to about 90%, based upon weight of the composition. In a preferred embodiment, the hydrating active ingredient is hydrating active ingredient is Aloe Barbadensis Leaf Juice.

Oil Phase

The oil phase present in the cosmetic composition according to the disclosure includes at least one fatty substance, at least one gelling agent, and at least one thickener.

Suitable fatty substances include oil(s) and/or wax(es). "Oil" means any non-aqueous medium which is liquid at ambient temperature (25° C.) and atmospheric pressure (760 mm Hg). Suitable oils include volatile and/or non-volatile oils. Such oils can be any acceptable oil including, but not limited to, silicone oils, hydrocarbon oils.

Among the oils that can form part of the composition of the oil phase, mention may be made especially of: mineral oils such as liquid paraffin and liquid petroleum jelly, oils of animal origin such as perhydrosqualene, oils of plant origin such as sweet almond oil, avocado oil, castor oil, olive oil, jojoba oil, sesame seed oil, groundnut oil, grapeseed oil, rapeseed oil, coconut oil, hazelnut oil, shea butter, palm oil, apricot kernel oil, beauty-leaf oil, rice bran oil, maize germ oil, wheatgerm oil, soybean oil, sunflower oil, evening primrose oil, safflower oil, passionflower oil and rye oil, synthetic oils such as purcellin oil, butyl myristate, isopropyl myristate, cetyl myristate, isopropyl palmitate, isopropyl adipate, ethylhexyl adipate, butyl stearate, hexadecyl stearate, isopropyl stearate, octyl stearate, isocetyl stearate, decyl oleate, hexyl laurate, propylene glycol dicaprylate and esters derived from lanolic acid, such as isopropyl lanolate and isocetyl lanolate, isoparaffins and poly-α-olefins.

The composition of the present disclosure may also contain cosmetically acceptable additives or adjuvants as well as cosmetic or dermatologic active agents. Representative additives and adjuvants include, for example, water-soluble or water-miscible solvents or co-solvents, dispersion enhancing agents, moisturizers, colorants, fillers, preservatives, antioxidants (e.g., EDTA, BHT, tocopherol), essential oils, fragrances, dyes, neutralizing or pH-adjusting agents (e.g., triethylamine (TEA) and sodium hydroxide), conditioning or softening agents (e.g., panthenol, allantoin and glycerin) and extracts such as botanical extracts. Additives and adjuvants may be present in the compositions in amounts generally ranging from about 0.01% to about 10% by weight. Examples of cosmetic active agents or dermatological active agents include sunscreen agents (e.g., inorganic sunscreen agent, such as titanium dioxide and zinc oxide and organic sunscreen agents, such as octocrylene, ethylhexyl methoxycinnamate, and avobenzone), free-radical scavengers, keratolytic agents, vitamins (e.g., Vitamin E and derivatives thereof), anti-elastase and anti-collagenase agents, peptides, fatty acid derivatives, steroids, trace elements, extracts of algae and of planktons, enzymes and coenzymes, flavonoids and ceramides, hydroxy acids and mixtures thereof, and enhancing agents. These ingredients may be soluble or dispersible in whatever phase or phases is/are present in the cosmetic composition (i.e., aqueous and/or fatty (oil) phase).

Process

The method for preparing the cosmetic composition of the present disclosure, according to one embodiment, includes creating a stable oil-in-water emulsion without heating. The process uses a cold-processing method which keeps the temperature below 30° C. and more preferably at ambient temperature during emulsification. The process includes mixing a first phase (aqueous) including at least one hydrating active ingredient, at ambient temperature (about 25° C. and less than 30° C.). The process includes mixing a second phase including the fatty phase and at least one gelling-agent and at least one thickener at ambient temperature (about 25° C. and less than 30° C.). The process includes pouring the mixed second phase into the first mixed phase (aqueous). The process includes homogenizing the mixed first phase and the mixed second phase forming an oil-in-water emulsion without heat and at ambient temperature (about 25° C. and less than 30° C.). The process optionally includes adding arginine to the emulsion at ambient temperature (about 25° C. and less than 30° C.).

A method for treating keratinous tissue includes applying to the keratinous tissue the cosmetic composition of the present disclosure. The cosmetic composition of the present disclosure is in any desirable cosmetic form, such as, but not limited to, liquid lotions, creams, and mousses, can be applied to keratinous tissue to provide a greater hydration index than that of formulations containing only water and no aloe vera.

The following examples are intended to further illustrate the present invention. They are not intended to limit the invention in any way. Unless otherwise indicated, all parts are by weight.

EXAMPLES

TABLE 1

| Phase | Ingredient (INCI Name) | Reference Examples | | | | | |
|---|---|---|---|---|---|---|---|
| | | 1 | 2 | 3 | 4 | 5 | 6 |
| A | Caprylyl Glycol | 0.44% | 0.43% | 0.44% | 0.42% | 0.44% | 0.44% |
| A | Aloe Barbadensis Leaf Juice | 87.53% | 85.38% | 87.44% | 85.20% | 87.05% | 87.05% |
| A | Glycerin | 6.01% | 5.86% | 6.01% | 5.86% | 5.98% | 5.98% |
| A | Panthenol | 0.11% | 0.11% | 0.11% | 0.11% | 0.11% | 0.11% |
| B | Oil/Fatty Substance | 4.05% | 3.95% | 4.04% | 3.94% | 4.03% | 4.03% |
| B | Carbomer | 0.77% | | | | | |
| B | Acrylates/C10-30 Alkyl Acrylate Crosspolymer | | | | 0.87% | | |
| B | Sodium Acrylate/Sodium Acryloyldimethyl Taurate Copolymer and Sorbitan Laurate | | 3.2% | | | | |
| B | Acrylamide/Sodium Acryloyldimethyltaurate copolymer | | | | | 3.41% | |
| B | Ammonium Polyacryloyldimethyl Taurate (97.4%) | | | | | 1.31% | |
| B | Ammonium Acryloyldimethyltaurate/VP Copolymer (95%) | | | | | | 1.31% |
| C | Arginine | 1.09% | 1.07% | 1.09% | 1.06% | 1.09% | 1.09% |
| | Total (wt %) | 100.00% | 100.00% | 100.00% | 100.00% | 100.00% | 100.00% |
| | Viscosity (3, 10 mins.) (mPa·s) | Unmeasurable too low to read | 8.7 | Unmeasurable too low to read | Unmeasurable too low to read | 11.7 | 10 |
| | Appearance | water fluidity | liquid lotion | separated unstable | water fluid | lotion | water unstable |

*** Brookfield RVF Viscometer: W/O measured with Spindle No. 3 at 10 rpm at 25° C. O/W measured with Spindle No. 3 at 10 rpm at 25° C.

TABLE 2

| Phase | Ingredient (INCI Name) | Examples | | | | |
|---|---|---|---|---|---|---|
| | | 1A | 2A | 3A | 4A | 5A |
| A | Caprylyl Glycol | 0.42% | 0.42% | 0.42% | 0.43% | 0.43% |
| A | Aloe Barbadensis Leaf Juice | 84.74% | 84.65% | 84.57% | 86.38% | 86.38% |
| A | Glycerin | 5.83% | 5.82% | 5.81% | 5.94% | 5.94% |
| A | Panthenol | 0.11% | 0.11% | 0.11% | 0.11% | 0.11% |
| B | Oil/Fatty Substance | 3.92% | 3.92% | 3.91% | 4.00% | 4.00% |
| B | Carbomer | 0.74% | — | 0.74% | 0.76% | 0.76% |
| B | Acrylates/C10-30 Alkyl Acrylate Crosspolymer | — | 0.85% | — | — | — |
| B | Sodium Acrylate/Sodium Acryloyldimethyl Taurate Copolymer and Sorbitan Laurate | 3.18% | 3.17% | — | — | — |
| B | Acrylamide/Sodium Acryloyldimethyltaurate copolymer | — | — | 3.38% | — | — |
| B | Ammonium Polyacryloyldimethyl Taurate (97.4%) | — | — | — | 1.30% | — |
| B | Ammonium Acryloyldimethyltaurate/VP Copolymer (95%) | — | — | — | — | 1.30% |
| C | Arginine | 1.06% | 1.06% | 1.06% | 1.08% | 1.08% |
| | Total (wt %) | 100.00% | 100.00% | 100.00% | 100.00% | 100.00% |
| | Viscosity (3, 10 mins.) (mPa·s) | 84.5 | 98.9 | 101 | 80.8 | 58.8 |
| | Appearance | cream | cream | cream | cream | cream |

*** Brookfield RVF Viscometer: W/O measured with Spindle No. 3 at 10 rpm at 25° C. O/W measured with Spindle No. 3 at 10 rpm at 25° C.

The method of making each of the examples provided in Tables 1 and 2 is generally the same. The examples in Table 1 are reference examples and the examples in Table 2 are the examples according to an embodiment of the present disclosure.

In making each of the examples in Tables 1 and 2, the following procedures were followed. The ingredients of Phase A (aqueous phase) were added to the main kettle and mixed at ambient temperature. The ingredients of Phase B (oil phase) mixed in a side kettle at ambient temperature. Next, the contents of the Phase A (aqueous phase) and Phase B (oil phase) were combined and sheared. During shearing, the phases were emulsified, and the temperature of the ingredients was monitored and controlled to ensure homogenous mixing at ambient temperature and that the temperature of the ingredients did not exceed excessive temperatures due to mechanical shear.

Phase C, the arginine, was added to the kettle and mixed to obtain the various compositions described above in Tables 1 and 2.

Reference Examples 1-6 include caprylyl glycol, Aloe Barbadensis Leaf Juice, glycerin, pantenol, and either a gelling agent or a thickener. Reference Examples 1-6 highlight the instability of the emulsion created using only the gelling agent or thickener and the low or the unmeasureable viscosities of the resultant compositions. The viscosities of Reference Examples 1, 3 and 4 were unmeasurable because the force of the resultant formulations were too marginal to be read by the viscometer used.

Examples 1a-5a, according to the present disclosure, include caprylyl glycol, Aloe Barbadensis Leaf Juice, glycerin, pantenol, and both a gelling agent and a thickener. Examples 1a-5a provide stable emulsions in a cream form with desired viscosity properties. It has been surprisingly discovered by the inventors that the combination of the gelling agent and thickener results in a stable cream composition having a higher viscosity than that of the examples having only the gelling agent or only the thickener.

Reference Example 1 includes only the gelling agent carbomer and results in a composition having an unmeasurable viscosity and an appearance of water fluidity, unsuitable for use in cosmetic compositions. Reference Example 2 includes only the thickener sodium acrylate/sodium acryloyldimethyl taurate copolymer and sorbitan laurate and results in a composition having a viscosity of 8.7 mPa·s and a liquid lotion appearance. In contrast, Example 1a, according to the present disclosure, includes the gelling agent carbomer and the thickener sodium acrylate/sodium acryloyldimethyl taurate copolymer and sorbitan laurate. Surprisingly, the cosmetic composition formed from Example 1a has a viscosity of about 84.5 mPa·s and forms a cream composition.

Reference Example 3 includes only the gelling agent acrylates/C10-30 alkyl acrylate crosspolymer and results in a composition having an unmeasureable viscosity and non-emulsion. The composition of Reference Example 3 is a separated composition, having a separate aqueous phase and a separate oil phase, which is undesirable. In contrast Example 2a, according to the present invention, includes acrylates/C10-30 alkyl acrylate crosspolymer as the gelling agent and sodium acrylate/sodium acryloyldimethyl taurate copolymer and sorbitan laurate as the thickener. Surprisingly, the cosmetic composition formed from Example 2a has viscosity of about 98.9 mPa·s and forms a cream composition.

Reference Example 4 includes only the thickener acrylamide/sodium acryloyldimethyltaurate copolymer and results in a composition having an unmeasurable viscosity and being in the form of a water fluid, unsuitable for use in cosmetic compositions. In contrast, Example 3a, according to the present invention, includes a carbomer as a gelling agent and acrylamide/sodium acryloyldimethyltaurate copolymer as the thickener. Surprisingly, the cosmetic composition formed from Example 3a has a viscosity of about 101 mPa·s and forms a cream composition.

Reference Example 5 includes only the thickener ammonium polyacryloyldimethyl taurate (97.4%) and results in a composition having a viscosity of about 11.7 mPa·s and in the form of a lotion. In contrast, Example 4a, according to the present invention, includes a carbomer as a gelling agent and ammonium polyacryloyldimethyl taurate (97.4%) as the thickener. Surprisingly, the cosmetic composition formed from Example 4a has a viscosity of about 80.8 mPa·s and forms a clear cream composition.

Reference Example 6 includes only the thickener ammonium acryloyldimethyltaurate/VP copolymer (95%) and results in a composition having a viscosity of about 10 mPa·s and in the form of a water unstable emulsion. In contrast, Example 5a, according to the present invention, includes a carbomer as a gelling agent and ammonium acryloyldimethyltaurate/VP copolymer (95%) as the thickener. Surprisingly, the cosmetic composition formed from Example 5a has a viscosity of about 58.8 mPa·s and forms a stable cream composition.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A cosmetic composition in the form of an emulsion comprising:
    a hydrating active ingredient, the hydrating active ingredient being 1x concentration of Aloe Barbadensis Leaf Juice at a concentration, by weight, of about 80% to about 90%, based upon weight of the composition;
    added arginine;
    at least one gelling agent, the at least one gelling agent at a concentration, by weight, of about 0.01% to about 5%, based upon weight of the composition; and
    at least one thickener, the at least one thickener at a concentration, by weight, of about 0.1% to about 5%, based upon weight of the composition,
    wherein the composition is free of surfactants.

2. The cosmetic composition of claim 1, further comprising water.

3. The cosmetic composition of claim 1, wherein the at least one gelling agent comprises carbomer, acrylates/C10-30 alkyl acrylate crosspolymer, and combinations thereof.

4. The cosmetic composition of claim 1, wherein the at least one thickener comprises sodium acrylate/sodium acryloyldimethyl taurate copolymer, acrylamide/sodium acryloyldimethyltaurate copolymer, ammonium polyacryloyldimethyl taurate, ammonium acryloydimethyl taurate/VP Copolymer, and combinations thereof.

5. The cosmetic composition of claim 1, wherein the arginine is at a concentration, by weight, of about 0.05% to about 1.5%, based upon weight of the composition.

6. The cosmetic composition of claim 1, wherein the composition has a viscosity of about 25 mPa·s to about 105 mPa·s.

7. The cosmetic composition of claim 1, wherein the composition is free of emulsifiers.

8. The cosmetic composition of claim 1, wherein the composition is free of parabens.

9. The cosmetic composition of claim 1, wherein the composition has a lower surface tension than water and allows for greater pore penetration than water.

10. A method for preparing the cosmetic composition of claim 1, comprising:
    mixing a first phase including the hydrating active at ambient temperature;
    mixing a second phase including the at least one gelling-agent and at least one thickener at ambient temperature;
    homogenizing the mixed first phase and the mixed second phase forming an oil-in-water emulsion at ambient temperature; and
    wherein the temperature of the composition during mixing and homogenizing does not exceed about 30° C.

11. A method for cosmetic treatment of keratinous tissues, comprising applying the cosmetic composition according to claim 1.

\* \* \* \* \*